United States Patent

Gutman

[11] 4,010,263
[45] Mar. 1, 1977

[54] INSECTICIDAL ACTIVE THIOPHENE PHOSPHOROUS DERIVATIVES

[75] Inventor: Arnold D. Gutman, Berkeley, Calif.

[73] Assignee: Stauffer Chemical Company, Westport, Conn.

[22] Filed: May 5, 1975

[21] Appl. No.: 574,781

Related U.S. Application Data

[60] Continuation-in-part of Ser. No. 406,042, Oct. 12, 1973, abandoned, which is a continuation-in-part of Ser. No. 325,491, Jan. 22, 1973, abandoned, which is a division of Ser. No. 179,233, Sept. 9, 1971, abandoned.

[52] U.S. Cl. ............................ 424/202; 260/329 P; 260/940
[51] Int. Cl.² .......................................... A01N 9/36
[58] Field of Search ............... 424/202; 260/329 D, 260/940

[56] References Cited

UNITED STATES PATENTS

| | | |
|---|---|---|
| 2,957,007 | 10/1960 | McCall et al. ................. 260/332.5 |
| 3,462,439 | 8/1969 | Popoff et al. ...................... 260/290 |
| 3,639,537 | 2/1972 | Kaufman ........................... 260/940 |
| 3,652,741 | 3/1972 | Montgomery et al. ............ 260/956 |

Primary Examiner—Albert T. Meyers
Assistant Examiner—D. W. Robinson
Attorney, Agent, or Firm—Edith A. Rice; Daniel C. Block

[57] ABSTRACT

Thiophene phosphorous derivatives and their use as insecticides are described herein. The compounds are defined by the following formula:

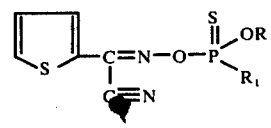

wherein R is a lower alkyl group having from 1 to 4 carbon atoms and $R_1$ is selected from lower alkyl and lower alkoxy having from 1 to 4 carbon atoms.

4 Claims, No Drawings

INSECTICIDAL ACTIVE THIOPHENE PHOSPHOROUS DERIVATIVES

CROSS-REFERENCE TO RELATED APPLICATION

This is a Continuation-In-Part of U.S. Pat. application Ser. No. 406,042, filed Oct. 12, 1973, now abandoned which is a Continuation-In-Part of U.S. Pat. application Ser. No. 325,491, filed Jan. 22, 1973, now abandoned, which is a division of application Ser. No. 179,233, filed Sept. 9, 1971, now abandoned.

DESCRIPTION OF THE INVENTION

This invention is directed to a group of compounds which may be generically described as thiophene glyoxylonitrile oxime phosphorous derivatives which are active insecticides.

The compounds of the present invention are represented by the general formula

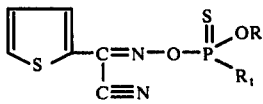

wherein R is a lower alkyl group having from 1 to 4 carbon atoms and $R_1$ is selected from lower alkyl and lower alkoxy having from 1 to 4 carbon atoms. The above compounds can be prepared by treating thiophene glyoxylonitrile oxime sodium salt with a dialkyl phosphoryl halide or an alkoxy, alkyl phosphonyl halide. The thiophene glyoxylonitrile oxime sodium salt can be synthesized by treating sodium methoxide with a mixture of thiophene acetonitrile and amyl nitrite in the presence of a solvent. These compounds have shown selective insecticidal activity for the insect orders Diptera, Hemiptera, Homoptera, Orthoptera, Coleoptera and Lepidoptera selected from Cabbage Looper [Trichoplusia ni (Hübner)] and Beet Armyworm [Spodoptera exigua (Hübner)].

In order to illustrate the merits of the present invention, the following examples are provide.

EXAMPLE 1

Synthesis of thiophene-2-glyoxylonitrile oxime sodium salt.

—45.3 g. (0.21 moles) of 25% sodium methoxide solution in methanol and 200 ml. of methanol were combined in a 500 ml. three-necked flask fitted with a stirrer, thermometer, dropping funnel and condenser fitted with a calcium chloride drying tube. The solution was stirred and cooled in an ice bath at 10° C. A mixture of 24.6 g. (0.21 moles) of isoamylnitrate and 24.6 g. (0.2 moles) of thiophene-2-acetonitrile was added through the dropping funnel at such a rate that the reaction temperature does not exceed 15° C. After the addition was complete, the ice bath was removed and the reaction mass was stirred for four hours at room temperature. The reaction mass was then stripped in vacuo of all volatiles. The residue was titrated with 300 ml. of anhydrous diethylether, and the desired product was collected by filtration.

EXAMPLE 2

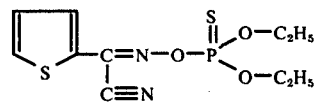

8.3 g. (0.05 moles) of thiophene-2-glyoxylonitrile oxime sodium salt was dissolved in 150 ml. of acetone in a 250 ml. flask. Then, 9.4 g. (0.05 moles) of 0,0-diethylthiophosphoryl chloride was added and there was an immediate precipitation of salt. The reaction mass was allowed to stand at room temperature for one hour. Then it was poured into 300 ml. of benzene. The benzene mixture was washed with three 200 ml. portions of water, dried with anhydrous magnesium sulfate, and evaporated in vacuo to yield 13.5 g. (99% of theory) of the desired product. $n_D^{30}$ — 1.5372.

EXAMPLE 3

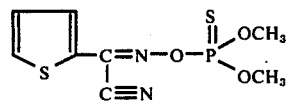

In a similar manner as set forth in Example 2, 8.2 g. (0.05 moles) of thiophene-2-glyoxylonitrile oxime sodium salt was combined with 8.2 g. (0.05 moles) of 0,0-dimethylthiophosphoryl chloride to produce the desired product. $n_D^{30}$ — 1.5517.

EXAMPLE 4

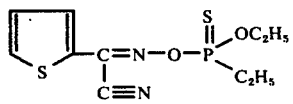

In a similar manner as set forth in Example 2, 8.3 g. (0.05 moles) of thiophene-2-glyoxylonitrile oxime sodium salt was combined with 8.6 g. (0.05 mole) of O-ethyl, ethyle thiophosphorylchloride to produce 12.5 g. of the desired product. $n_D^{30}$ — 1.5665.

Additional prior art compounds were made according to known procedures. These compounds are listed in the following examples:

Example 5*

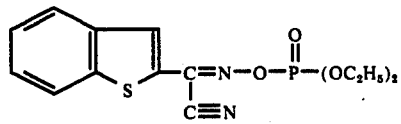

Example 6*

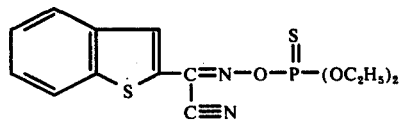

Example 7*

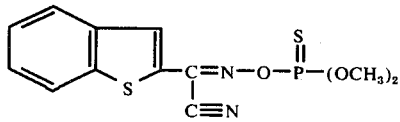

*See U.S. Patent 3,639,537 - Kaufman

The following test methods were used to illustrate the insecticidal activity of the compounds of this invention:

I. Diptera
  A. House Fly [Musca domestica (L.)] (HF)
    1. Film residue

A stock solution containing 100 μg/ml. of the toxicant in an appropriate solvent is prepared. Aliquots of this solution are combined with 1 ml. of an acetone-peanut oil solution in a dish, 55 mm. in diameter, and allowed to dry. The aliquots are varied to achieve desired toxicant concentrations ranging from 100 μg per dish to that at which 50% mortality is obtained. The dishes are placed in a circular cardboard cage, closed on the bottom with cellophane and covered on top with cloth netting. Twenty-five female house flies are introduced into the cage and the percent mortality is recorded after 48 hours. LD-50 values are expressed in terms of μg per female flies.

2. Soil

Test compounds are diluted in acetone as noted above and aliquots are thoroughly incorporated into 250 grams of moist sandy loam soil. Twenty-five five-day-old housefly larvae are introduced into the treated soil. Forty-eight hours later the larvae and/or pupae are retrieved from the soil, placed on a piece of moist filter paper in a Petri dish, and held until the adult flies have emerged from the pupal cases. Mortality is determined by the percentage of adult flies failing to emerge. Tests concentrations range from 10 PPM in the soil down to that at which 50% mortality occurs.

B. Mosquito [Culex pipiens quinquefasciates] (MOS)

100 ml. of an aqueous solution of the test compound, at a concentration of 0.5 PPM, are placed in a 6 ounce, number 67 Dixie wax paper cup, Ten late third or early forth instar larvae of the mosquito Culex pipiens quinquefasciates are placed in each cup and the cups are stored at 70° F. for three days, at which time mortality counts are made. Compounds which are active at 0.5 PPM are retested at progressively lower concentrations until and LD-50 value is determined.

II. Orthoptera
  A. German Cockroah [Blattella germanica (Linne)] (GR)

Ten one-month-old nymphs are placed into a circular cardboard cage sealed on one end with cellophane and covered by cloth netting on the other. Aliquots of the toxicant, dissolved in an appropriate solvent, are diluted in water to which has been added 0.0002% of a conventional wetting agent such as polyoxy-ethylene sorbitan monolaurate ether of alkylated phenols blended with organic sulfonates. Test concentrations range from 0.1% to that at which 50% mortality is obtained. Each of these aqueous suspensions are sprayed onto the insects, through the cloth netting, by means of a hand spray gun. Percent mortality is recorded after 72 hours and the LD-50 values are expressed as percent of toxicant in the aqueous spray.

III. Hemiptera
  A. Milkweed Bug [Oncopeltus fasciatus (Dallas)] (MWB)

Test compounds are diluted in a 50—50 acetone-water solution. Two cc of the solutions are sprayed through a DeVilbiss type EGA hand spray gun into circular cardboard cages containing ten two-week-old milkweed bug nymphs. The test cages are covered on the bottom with cellophane and the top with tulle netting. Percent mortality is recorded 48 hours later. Test concentrations range from 0.1% down to that at which approximately 50% mortality occurs.

B. Lygus Bug [Lygus hesperus (Knight)] (LB)

Same as for the German cockroach (II A) except that the test concentrations range from 0.05% to that at which 50% mortality is obtained.

IV. Homoptera
  A. Black Bean Aphid [Aphis fabae (Scop.)] (BA)

Nasturtium (Tropaeolum sp.) plants, approximately 2–3 inches tall, are transplanted into sandy loam soil in 3 inch clay pots and infested with 50–75 aphids of mixed ages. Twenty-four hours later they are sprayed, to the point of runoff, with aqueous suspensions of the toxicant. The suspensions are prepared as in previously described tests. Test concentrations ranged from 0.05% to that at which 50% mortality is obtained. Mortality is recorded after 48 hours and the LD-50 values are expressed as percent active ingredient in the aqueous suspensions.

V. Coleoptera
  A. Spotted Cucumber Beetle Larvae [Diabrotica undecimpunctata (Mannerheim)] (CB)

One cc of eggs contain about 7,000 eggs. These are diluted to a final concentration of 250 eggs/cc by suspending 0.5 cc of undiluted eggs in 14 cc of water containing 0.2% of a conventional gel. Eggs may be stored in this suspension for 5 days at 5° C. without significant loss of viability. Seven and one-half grams of sterile, slightly moist soil are placed in a 1 oz. clear plastic cup. The test chemicals, dissolved in 0.1 ml. of acetone, are then added to the soil. The cups are capped, placed in a closed plastic tub and tumbled for 10 minutes. A ¼ inch hole is then punched in each cap, and 2-½ cc of water and 0.2 cc of the egg suspension are added to the soil. The treated cups are maintained at 80° F. and 40% R.H. for 5 days, at which time a section of Romaine lettuce leaf is placed in each cup. Five days later the cups are examined for live larve. Test concentrations range from 10 PPM down to that at which approximately 50% mortality occurs.

VI. Lepidoptera
  A. Salt-marsh Caterpillar [Estigmene acrea (Drury)] (SMC)

Test solutions are prepared in an identical manner and concentrations are the same as those for the German cockroach (II A). Sections of bitter dock (Rumex obtusifolius) leaves, 1–1.5 inches in length are immersed in the test solutions for 10–15 seconds and placed on a wire screen to dry. The dried leaf is placed on a moistened piece of filter paper in a petri dish and infested with five third-instar larvae. Mortality of the larvae is recorded after 72 hours and the LD-50 values are expressed as percent active ingredient in the aqueous suspensions.

B. Tobacco Budworm [Heliothis virescens (F.)] (TBW)

Same as for the Salt-marsh caterpillar (VI A) except that leaves of Romaine lettuce (*Latuca sativa*) are utilized as the host plane rather than bitter dock.

C. Beet Armyworm (Spodoptera exigua (Hübner) (BAW)

Same as the Salt-marsh caterpillar (VI A) except that leaves of Romaine lettuce (*Latuca sativa*) are utilized as the host plant rather than bitter dock.

D. Cabbage Looper Larvae [*Trichoplusia ni* (Hübner) (CL)]

Test compounds are diluted in a 50—50 acetone-water solution. Cotyledons of hyzini squash (*Calabacita abobrinha*), approximately 1×1.5 inches, are immersed in the test solutions for 2–3 seconds and placed on a wire screen to dry. The dried leaves are placed in petri dishes containing a moistened piece of filter paper and infested with five second-instar cabbage looper larvae. Mortality of the larvae is recorded 48 hours later, and a piece of synthetic media is added to dishes containing survivors. These are then held for five additional days to observe for any delayed effects of the test chemicals. Test concentrations range from 0.1% to that at which approximately 50% mortality occurs.

TABLE

| Compound No. | Diptera HF Residue | Diptera HF Soil | MOS | Orthoptera GR | Hemiptera LB | Hemiptera MWB | Homoptera BA | Coleoptera CB | Lepidoptera SMC | Lepidoptera TBW | Lepidoptera BAW | Lepidoptera CL |
|---|---|---|---|---|---|---|---|---|---|---|---|---|
| 2 | 30 | 3 | 0.03 | 0.02 | 0.0008 | 0.008 | 0.008 | 2 | 0.03 | 0.05 | 0.005 | 0.005 |
| 3 | 25 | 3 | 0.008 | 0.08 | 0.0008 | >0.05 | 0.008 | >10 | 0.05 | 0.03 | 0.01 | .08 |
| 4 | 10 | 3 | 0.05 | 0.005 | 0.002 | 0.025 | 0.002 | 2 | 0.03 | 0.05 | 0.03 | .008 |
| 5 | >100 | >10 | >0.5 | >0.1 | 0.03 | >0.05 | 0.03 | >10 | 0.03 | 0.1 | >0.1 | >0.1 |
| 6 | 100 | >10 | >0.5 | >0.1 | >0.05 | >0.05 | >0.05 | 2 | 0.03 | — | 0.03 | 0.1 |
| 7 | 45 | >10 | 0.5 | >0.1 | >0.05 | >0.05 | >0.05 | >10 | >0.05 | — | >0.1 | 0.1 |

The compositions of this invention are generally embodied into a form suitable for convenient application. For example, the compositions can be embodied into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed as the sole pesticide component or they can be used in admixture with other compounds having similar utility. The pesticide formulations of this invention can contain, as adjuvants, organic solvents, such as sesame oil, xylene range solvents, heavy petroleum, etc; water; emulsifying agents; surface active agents; talc; pyrophyllite; diatomite; gypsum; clays; propellants, such as dichlorodifluoromethane, etc. If desired, however, the active compositions can be applied directly to feedstuffs, seeds, etc. upon which the pests feed. Then applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the compound is ingested into the body of the pest.

The precise manner in which the pesticidal compositions of the invention are used in any particular instance will be readily apparent to a person skilled in the art. Generally, the active pesticide composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

What is claimed is:

1. A method of killing insects selected from the insect orders of Diptera, Orthoptera, Hemiptera, Homoptera, Coleoptera and Lepidoptera selected from the group consisting of Cabbage Looper and Beet Armyworm comprising applying to the habitat thereof an insecticidally effective amount of a compound of the formula

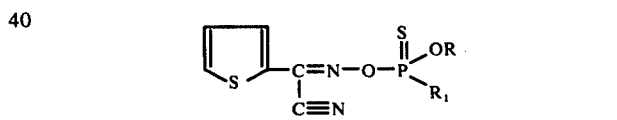

wherein R is a lower alkyl group having from 1 to 4 carbon atoms and $R_1$ is selected from the group of lower alkyl and lower alkoxy having from 1 to 4 carbon atoms.

2. A method of claim 1 wherein R is methyl and $R_1$ is methoxy.

3. A method of claim 1 wherein R is ethyl and $R_1$ is ethoxy.

4. A method of claim 1 wherein R is ethyl and $R_1$ is ethyl.

* * * * *